(12) United States Patent
Malyszewicz

(10) Patent No.: US 7,915,216 B2
(45) Date of Patent: Mar. 29, 2011

(54) ANTI-VIRAL AND ANTI-BACTERIAL CLEANING COMPOSITION

(75) Inventor: Christopher Malyszewicz, Northampton (GB)

(73) Assignee: Medigreen OOD, Sofia (BG)

( * ) Notice: Subject to any disclaimer, the term of this patent is extended or adjusted under 35 U.S.C. 154(b) by 4 days.

(21) Appl. No.: 10/556,481

(22) PCT Filed: May 17, 2004

(86) PCT No.: PCT/GB2004/002148
§ 371 (c)(1), (2), (4) Date: Nov. 14, 2005

(87) PCT Pub. No.: WO2004/101726
PCT Pub. Date: Nov. 25, 2004

(65) Prior Publication Data
US 2006/0286135 A1    Dec. 21, 2006

(30) Foreign Application Priority Data
May 15, 2003    (GB) .................................. 0311174.7

(51) Int. Cl.
*C11D 1/94* (2006.01)
(52) U.S. Cl. ...................................................... 510/499
(58) Field of Classification Search .................... 510/499
See application file for complete search history.

(56) References Cited

U.S. PATENT DOCUMENTS

| | | | | |
|---|---|---|---|---|
| 4,832,950 | A | 5/1989 | Takaya et al. | 424/81 |
| 5,373,016 | A | 12/1994 | Brown et al. | 514/372 |

FOREIGN PATENT DOCUMENTS

| | | |
|---|---|---|
| DE | 4311535 | 3/1994 |
| DE | 19918475 | 10/2000 |
| JP | 58-057302 | 4/1983 |
| JP | 01-290608 | 11/1989 |
| JP | 09-322928 | 12/1997 |
| WO | WO 93/07250 | 4/1993 |
| WO | WO 00/18867 | 4/2000 |
| WO | WO 2005/089820 | 9/2005 |

OTHER PUBLICATIONS

Triameen T Product Literature, Akzo Nobel Surface Chemistry AB, Stenungsund, Sweden, Jun. 25, 2002.*
International Search Report and Written Opinion from corresponding International Application No. PCT/GB2004/002148.
1,2-Benzisothiazolin-3-one, www.dermacom.ch/private/alindex/BE000.htm (Sep. 30, 2009).
1,2-benzisothiazolin-3-one, pp. 1-7, downloaded from the Internet on Dec. 2, 2010 at http://sitem.herts.ac.uk/aeru/footprint/en/Reports/1361.htm , Environmental Fate—Ecotoxicology—Human Heath—A to Z Index, The PPDB web site.
EU Safety Phrases, Document No. PPDB 5.0, Version: Apr. 2009, pp. 1-3, downloaded from the Internet on Dec. 2, 2010 at http://sitem.herts.ac.uk/aeru/footprint/en/docs/EU_Safety_Phases_UH.pdf.

(Continued)

*Primary Examiner* — John R Hardee
(74) *Attorney, Agent, or Firm* — Greenberg Traurig LLP

(57) ABSTRACT

A composition comprising at least one alcohol, at least one long-chain alkyl polyamine, and at least one halogen which is suitably for application to a surface and substantially microbial contamination.

15 Claims, 2 Drawing Sheets

OTHER PUBLICATIONS

List of compilation of Adaptations to Technical Progress up to ATP 29, published in OJL 152 of Apr. 30, 2004, pp. 1 and 237, downloaded from the Internet on Dec. 2, 2010 at http://www.greencouncil.org/doc/ResourcesCentre/annex1.pdf.

Council Directive 67/548/EEC of Jun. 27, 1967 on the approximation of laws, regulations and administrative provsions relatein to the classification, packaging and labeling of dangerous substances, Official Journal 196, 1967, Aug. 16, 1967, pp. 1-4, downloaded from the Internet on Dec. 2, 2010 at http://eur-lex.europa.eu/LexUriServ/LexUriServ.do?uri=CELEX:31967L0548:EN:HTML.

Office Action, dated Nov. 2, 2010, from corresponding, co-owned Canadian Patent Application No. 2,525,705.

Office Action, dated Nov. 2, 2010, from corresponding, co-owned Japanese Patent Application No. 2006-530514.

* cited by examiner $H_2N(CH_2)_3 - NR - (CH_2)_3 NH_2$ where $R = C_{12}$ $$\begin{array}{c} (CH_2)_3 NH_2 \\ | \\ N - R \\ | \\ (CH_2)_3 NH_2 \end{array}$$

where $R = C_{12}$

Fig. 2

ANTI-VIRAL AND ANTI-BACTERIAL CLEANING COMPOSITION

FIELD OF INVENTION

The present invention relates to a liquid cleansing composition having an anti-viral and/or anti-bacterial action. More particularly, but not exclusively, it relates to a surface cleansing composition having both anti-viral and anti-bacterial activity.

BACKGROUND

There is an ever expanding number of household products such as handwashes and domestic cleaning sprays professing to provide anti-bacterial properties. Often these products claim to eliminate work surfaces and the like of all known bacteria. Such claims are typically misleading at best. Widely reported research has shown that many of these currently available products are no better at reducing the onset of coughs, colds or other such infections or ailments than thoroughly washing one hands or cleaning the work surfaces. Indeed many such infections or aliments are caused by viruses which currently available anti-bacterial products are unable to combat, despite what they purport to achieve.

There is also an increasing concern about bacterial and viral infections being transmitted to patients and staff in hospitals and the like. One vector of infection is believed to be incompletely disinfected surfaces, which may harbour bacteria and/or viruses that are resistant to existing surface cleaning agents. There is a strong suspicion that the spread of the recent SARS (Severe Acute Respiratory Syndrome) outbreak may have been linked to the ability of the SARS virus to resist conventional cleaning agents/disinfectants. Viruses spread from an infected patient thus remain viable and ready to be picked up by and to infect other patients and medical staff. Other pathogens, such as the MRSA bacterium, are also suspected to be surviving existing surface cleaning/disinfecting agents and routines.

It is known to use cationic surfactants, such as quaternary ammonium salts, as dual-purpose surface cleaning agents and bactericides. However, while such materials are generally found to be sufficient to deal with, say, food-poisoning bacteria in a food preparation environment, they are not regarded as sufficiently active to handle more dangerous and more resistant pathogens in a medical context.

Alcohols, such as iso-propanol, and halogens, such as iodine, have in the past been used individually as relatively crude disinfecting agents around wounds and skin lesions, but they have not proven suitable for wide area cleaning of hard surfaces and the like. For example, iodine can stain many surfaces, and its use at high concentrations is limited by safety considerations.

It is an object of the present invention to provide a liquid cleansing and disinfecting preparation, suitable for use on hard surfaces, with a high anti-viral and anti-bacterial effectiveness.

SUMMARY OF INVENTION

According to a first aspect of the present invention there is provided a composition comprising at least one alcohol, at least one long-chain alkyl polyamine, and at least one halogen.

According to a second aspect of the present invention there is provided a composition for cleaning and disinfecting comprising at least one alcohol, at least one long-chain alkyl polyamine, and at least one halogen.

According to a third aspect of the present invention, there is provided an aqueous surface cleaning and disinfecting composition comprising at least one alcohol, at least one long-chain alkyl polyamine, and at least one halogen.

According to a fourth aspect of the present invention, there is provided an anti-bacterial composition comprising at least one alcohol, at least one long-chain alkyl polyamine, and at least one halogen.

According to a fifth aspect of the present invention, there is provided an anti-viral composition comprising at least one alcohol, at least one long-chain alkyl polyamine, and at least one halogen.

According to a sixth aspect of the present invention, there is provided an anti-fungal composition comprising at least one alcohol, at least one long-chain alkyl polyamine, and at least one halogen.

According to an seventh aspect of the present invention, there is provided a means of destroying organisms and/or inhibiting the ability of bacteria and/or viruses to replicate when said bacteria and/or viruses are present on a surface, the means comprising the application of a composition to said surface wherein the composition is configured to rupture the phospholipid membrane of the bacteria or virus, the composition being further configured to substantially permanently bind to bacterial DNA and viral DNA or RNA. In this context "substantially permanently" is understood to mean that the bacterial DNA or viral DNA or RNA has a component or components of the composition bound thereto such that said DNA or RNA is unable to replicate for at least several hours, but preferably indefinitely. These means advantageously allow for rapid decontamination of a surface. Preferably the composition comprises at least one alcohol, at least one long-chain alkyl polyamine, and at least one halogen. Most preferably the composition is substantially as described in the other aspects of the present invention.

According to a eighth aspect of the present invention, there is provided a means of inhibiting the ability of bacteria and/or viruses to replicate when said bacteria and/or viruses are present on a surface, the means comprising the application of a composition to said surface wherein the composition is configured to substantially permanently encapsulate the bacterial or viral structures and prevent the replication of their genetic material. In this context "substantially permanently" is understood to mean that the bacteria or virus has a component or components of the composition bound thereto such that said DNA or RNA is encapsulated to the degree that it is unable to replicate for at least several hours, but preferably indefinitely. These means advantageously allow for rapid decontamination of a surface. Preferably the composition comprises at least one alcohol, at least one long-chain alkyl polyamine, and at least one halogen. Most preferably the composition is substantially as described in the other aspects of the present invention.

In the various aspects of the present invention, the long-chain alkyl polyamine compound preferably comprises a long-chain alkyl triamine compound and/or a long-chain alkyl tetramine compound.

The composition may comprise a mixture of long-chain alkyl polyamine compounds having a range of different alkyl chain lengths.

Advantageously, the long-chain alkyl polyamine compound may comprise a compound of the general formula [R—NH—$(CH_2)_m$—NH—$(CH_2)_n$—$NH_2$]$H_2$N$(CH_2)_3$—

NR—(CH$_2$)$_3$NH$_2$, where R is a linear or branched alkyl chain comprising at least eight carbon atoms, [and each of m and n may equal either 2 or 3].

R may be a linear or branched alkyl chain comprising between ten and fourteen carbon atoms. Preferably R is a linear alkyl chain, and [each of m and n may equal 3] comprises at least twelve carbon atoms.

The composition preferably comprises between 10% and 30% by volume of the long-chain alkyl polyamine compound or compounds.

Advantageously, the composition comprises between 15% and 25% of the long-chain alkyl polyamine compound or compounds. Optionally, the composition may comprise 20%±2% of the long-chain alkyl polyamine compound or compounds.

Preferably, the at least one aliphatic alcohol comprises between one and four carbon atoms.

The composition preferably comprises two aliphatic alcohols. It is particularly preferred that the composition comprises ethanol and n-propanol.

The composition may comprise between 10% and 30% by volume aliphatic alcohols. Advantageously, the composition comprises between 15% and 25% by volume aliphatic alcohols. The composition may comprise between 10% and 20% by volume ethanol and between 5% and 10% by volume n-propanol. Optionally, the composition may comprise between 14% and 16% by volume ethanol and between 5% and 7% by volume n-propanol.

Preferably the composition comprises a mixture of halogens and/or halogen source(s). Alternatively, the composition may comprise only a single halogen and/or single halogen source. The preferred halogen of the present invention is iodine, the preferred source of iodine being molecular iodine provided in a solid form.

The composition preferably comprises up to 0.5% by weight iodine. Advantageously, the composition may comprise between 0.1% and 0.5% by weight iodine. Optionally, the composition may comprise 0.33%±0.05% by weight iodine.

The composition may comprise a complexing agent adapted to form a complex with the halogen.

The composition may comprise at least one buffering agent, such as nitrilotriacetic acid or its salts.

The composition may comprise at least one surfactant. Preferrably at least one amphoteric surfactant is present in the composition. Ideally a mixture of amphoteric surfactants are present in the composition.

The composition may comprise at least one wetting agent, such as a polyglycol ether, optionally a polyethylene glycol ether or a polypropylene glycol ether.

The compositions of the present invention are preferably non-dangerous. In this context "non-dangerous" is understood to mean non-dangerous as defined by European Dangerous Preparations Directive (99/45/EC) and the Dangerous Substances Directive (67/548/EEC).

Although the composition is effective in a non-diluted form, there are numerous applications where a diluted composition would be desirable. The composition is preferably configured to be effective for a range of dilutions. For instance, the range for which the composition may be effective can be at any level of dilution with water up to a 1:1000 parts of water dilution. Normally the lower limit of dilution is a 1:1 dilution with water, but preferably the range of dilution for which the composition is effective is 1:5 parts of water to 1:100 parts of water dilution. The most preferred dilution however, is substantially 1 part of composition to substantially 9 parts of water.

The composition of the present invention may be provided in a form which is suitable for a number of different forms of delivery to a surface. The composition could be provided in a concentrated form for subsequent dilution by a user shortly before being used to clean a surface. Once diluted however, the resultant solution may be capable of being stored for up to 12 months and yet still being effective against bacteria and/or viruses and/or fungus and/or a provide a conventional detergent/cleansing effect which removes macroscopic soiling.

The composition of the present invention may be provided in a form ready for immediate delivery to a surface. The delivery device for such immediate delivery of the composition may be a controlled spray, such as a trigger spray or the like. A trigger spray advantageously allows a user to have a degree of remoteness from the surface the composition is to be used on, such that the composition may have already started to attack the bacteria and/or viruses present on said surfaces by the time the user comes into contact with the surface. Preferably the composition for immediate delivery is capable of being stored in its delivery device for up to 24 months and yet still being effective against bacteria and/or viruses and/or fungus and/or a provide a conventional detergent/cleansing effect which removes macroscopic soiling.

Another delivery device for immediate delivery of the composition of the present invention may be an impregnated cloth wipe. Such wipes could be provided in a container or drum containing numerous wipes, or provided in a single sachet form. Preferably such wipes are capable of being stored in their container for up to 24 months and yet still being effective against bacteria and/or viruses and/or fungus and/or a provide a conventional detergent/cleansing effect which removes macroscopic soiling.

According to a tenth aspect of the present invention there is provided a method for manufacturing a composition for cleaning and disinfecting wherein the method comprises: the addition to a pH buffered solution of at least one long-chain alkyl polyamine, to which is added at least one surfactant to make an interim solution; separate to said interim solution a premix solution containing at least one alcohol and at least one halogen is made; the interim solution and the premix solution are then combined.

According to a eleventh aspect of the present invention there is provided a composition comprising at least one alcohol, at least one long-chain alkyl polyamine.

According to a twelfth aspect of the present invention there is provided a composition comprising at least one long-chain alkyl polyamine and at least one halogen.

BRIEF DESCRIPTION OF THE DRAWINGS

In order to allow the present invention to be more readily understood an embodiment of the invention will now be described more particularly by way of example only, and with reference to the accompanying drawings in which:

FIG. 2 shows the chemical structure of the long-chain alkyl polyamine of the present invention.

Figure 1:
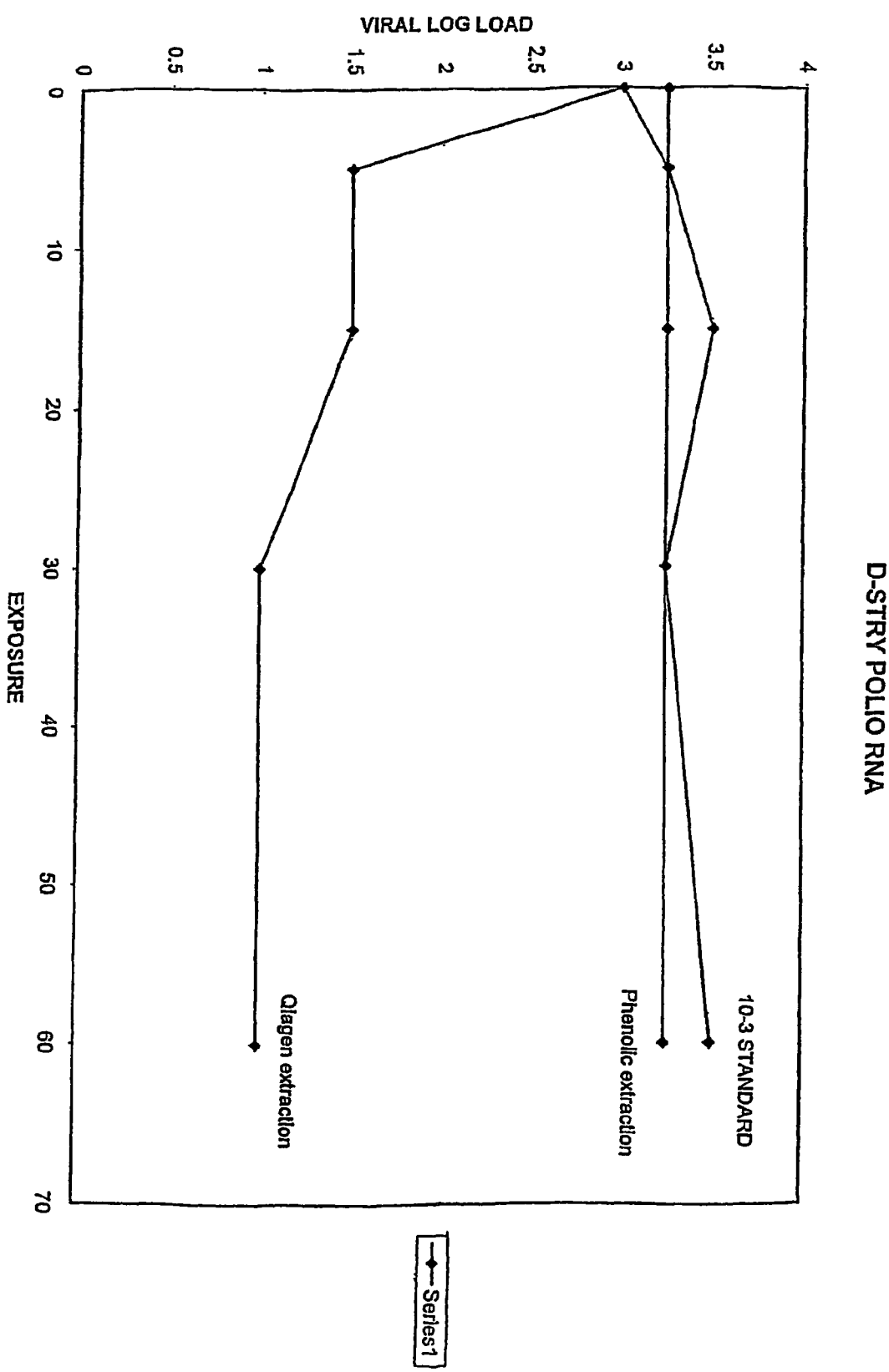
FIG. 1 shows a graph of the composition of the present invention's activity against Polio RNA.

An aqueous surface cleaning composition was prepared, comprising:

| | |
|---|---|
| NTA 89% powder | 0.85 kg |
| Ethanol | 15.0 litres |
| n-Propanol | 6.0 litres |
| Topanol O FG | 0.55 litres |

-continued

| Sandoteric SC | 2.42 litres |
| Sandozin NRW conc | 6.95 litres |
| Sandoteric ABD | 4.45 litres |
| Triameen Y12D-30 | 19.99 litres |
| Deionised water | 43.4524 litres |
| Iodine (solid) | 0.3376 kg |

The composition appeared as a pale yellow clear liquid with a pH of approximately 8 and a slight alcoholic odour.

SPECIFIC EMBODIMENTS

NTA is nitrilotriacetic acid trisodium salt, a buffering agent. Topanol O FG is food-grade butylated hydroxytoluene, an antioxidant, sold by Chance & Hunt Ltd. (Topanol is a registered trade mark of ICI plc). Sandozin NRW conc is a polyethoxylate ether sold by Clariant as a wetting agent. It also forms a relatively stable complex with iodine. Sandoteric SC is a sulphobetaine amphoteric surfactant, which acts as a detergent, and Sandoteric ABD is a complex mixture of amphoteric surfactants acting as a detergent and having a degree of bactericidal activity. Both are sold by Clariant. (Sandozin and Sandoteric are registered trade marks of Novartis SA).

Triameen Y12D-30 is a long-chain alkyl triamine of the general formula [R'—NH—$C_3H_6$—NH—$C_3H_6$—$NH_2$]$H_2$N$(CH_2)_3$—NR—$(CH_2)_3NH_2$, where R' is a "tallow alkyl"—a naturally-derived mixture of alkyl chains of different lengths, the most common of which is a dodecyl chain. It is sold by Akzo Nobel.

FIG. 2 illustrates the hypothesised structure of the long-chain alkyl triamine. It is possible that the activity of this molecule is located on the $NH_2$ groups, the iodine being monotonically bonded to the nitrogen yet accessible toward DNA or RNA. The nucleotides of the DNA or RNA may then be liganded by addition to phosphatide groupings by the presence of the iodated amine group. Thus, the iodine radical may be free to roam on the molecule and as there is partial addition thereof, there is competition for valencey fulfillment.

Although the mechanism of attack on bacterium is not fully understood, it is expected that in a suitably buffered solution the long-chain alkyl triamine forms a cationic species. Together with the surfactant(s), preferably amphoteric in nature, the triamine attacks the phospholipid membranes which form the outer wall of a bacterium. In most cases, these membranes are ruptured or lysed, leading to release of the bacterium's DNA. It is possible that the complexed halogen and the alcohol(s) act in conjunction on the DNA, effectively complexing with the DNA or RNA. The triamine and the surfactant(s) are believed to attack bacterial DNA and bind to critical parts of the helix preventing it from replicating. The alcohol(s) may also contribute to the attack on the membranes.

Even where the membranes are not sufficiently damaged to release their contents for destruction, the composition is found to inactivate the bacterium for prolonged periods (at least 14 days in current testing, much longer than for current cleaners/disinfectants).

Turning to the mechanism of attack on viruses, similarly this mechanism is also not fully understood. However it is again expected that the cationic triamine formed in a suitably buffered solution attacks the outer wall of the capsid of the virus in conjunction with the surfactant(s), which are preferably amphoteric in nature. It is possible that these structures are ruptured or lysed as a consequence of the attack, leading to release of the viral DNA or RNA. The complexed halogen and the alcohol(s) are believed to act in conjunction on viral DNA or by bonding or associating themselves with parts of the viral RNA. Additionally the triamine and the surfactant(s) are also believed to attack the viral DNA or RNA by binding to critical parts of the helix. The result of the attack(s) on the viral DNA or RNA is the inhibition of the DNA or RNA's ability to replicate. The alcohol(s) may also contribute to the attack on the membranes, particularly the outer viral phospholipid envelope, present in some but not all DNA/RNA viruses.

Alternatively, rather than the viral capsid being ruptured or lysed by the attack of the buffered cationic triamine and the surfactant(s), it is possible that the attack results in the binding to surface structures, blocking and inactivating viral receptors. The result of this attack being the inhibition of infectivity, thus preventing the virus spreading to other cells. It is possible that halogen and the alcohol(s) take some part in the attack of the viral capsid membrane.

Regardless of the mechanism, the combined action of the components of the composition is the break up and destruction of a majority of the organism and/or the inhibition of any viruses or bacteria for prolonged periods. The composition also has a conventional detergent/cleansing effect, removing macroscopic soiling from a surface to which it is applied, as well as washing off inhibited bacteria or viruses as well as the associated debris of the destroyed organism. The composition has been found to have minimal deleterious effect on the surfaces tested, and does not stain surfaces as would conventional formulations containing similar levels of halogen, particularly iodine.

As already mentioned, the mechanism of virucidal action by a composition of the present invention is not clearly understood. From the constituents present in the composition, it is suspected that the alcohol denatures proteins, and the quaternary ammonium compound(s) bind to anionic phosphate groups and fatty acid chains in phospholipids. Both mechanisms damage the microbial membranes. The halogen may modify structural proteins and may inhibit enzymes through halogenation of amino acids in proteins.

Through experimentation, various naked virus or purified animal deoxy-ribose nucleic acid (DNA) samples can be treated with the composition. An interaction takes place, so that when placed in an electric field under gel electrophoresis, a DNA smear is produced instead of the expected DNA ladder of normal integrity, indicating alteration of the ionisation characteristics of DNA. If the same composition/virus or composition/animal DNA mixture is extracted with a mixture of phenol/chloroform, the composition itself is broken down, and the full DNA electrophoretic pattern will be restored with normal integrity. This data indicates that the DNA (viral or animal DNA) is not degraded during the treatment with the composition, but that the composition interaction with viral or animal DNA alters the normal DNA structural and ionic integrity.

The interaction between the composition was further investigated for its affect on viral particles and viral ribose nucleic acid (RNA) and FIG. 1 illustrates the observed activity. Through experimentation where the composition (1 part in 10 parts water) as 9 part diluted composition and 1 part poliovirus vaccine (final 1000 copies/ml) for periods of 5, 15, 30 and 60 minutes, followed by extraction, using QIAGEN silicon columns (QIAGEN incorporates a protease step for protein degradation), prior to complimentary deoxy-ribose nucleic acid (cDNA) synthesis and DNA amplification, (with detection of nucleic acid product in a in-house real-time Lightcycler quantitative RNA assay), reductions in the RNA viral load can be seen from 1000 copies to 50, 50, 10, and 10 copies respectively-(reductions of 95%, 95%, 99%, 99%), compared to 1000, 1000, 1000, 1000 copies/ml respectively in water control samples. The experiment was repeated with composition/virus incubations of 5, 15, 30 and 60 minutes, as previously stated, but RNA extraction performed with a phenol/chloroform procedure (once with phenol, once with 1:1 phenol and chloroform, and once with chloroform rather than by the QIAGEN extraction method), RNA detection will be detected at 1000, 1000, 1000, and 1000 copies respectively (no reduction in RNA load).

The experiments demonstrate that the composition does not degrade RNA over the periods of 1-60 minutes, but that an interaction occurs between the composition and poliovirus/poliovirus RNA. This interaction inhibits protease action (active in the QIAGEN process) to cleave composition peptides that would normally release RNA, or alters naked RNA ionically, so that RNA cannot then be further captured and amplified in the test. The result is a low recovery of RNA, and will appear as a low copy number in the assay. The effect of the composition-virus interaction is removed during the chemical extraction with phenol. It can be concluded that the composition is not destructive to viral capsids, but inhibits enzymatic cleavage of the capsid, and requires further stringent chemical extraction to achieve release of the nucleic acid. The QIAGEN effect illustrated here is a consistent effect and has been replicated for other RNA and DNA viruses including Adenovirus, BK virus and Norovirus, and appears to be a plausible mechanism of virucidal activity, whereby the altered viral structure is resistance to physiological and enzymatic attack.

It can therefore finally concluded that both viral DNA and viral RNA is not degraded by treatment with the composition. However, the composition interacts with the viral capsid and prevents enzymatic cleavage. Although the process of virus uncoating involves different mechanisms for different virus groups, they all require the viral capsid to have structural and ionic integrity and be susceptible to cellular physiological processes that allow it to pass into and through the host cell, and interact with cellular structures and enzyme systems. The changes induced by the composition on viral structures are likely to prevent this process and account for its virucidal activity.

It is hypothesised that compositions with higher levels of halogen may be useful in some applications, although alterations to the other components, such as raised amounts of alcohol(s), may then be needed for stability.

The composition also has a degree of activity against fungi, moulds and yeasts, although it is believed that a modified formulation, for example with an alternative alcohol blend, might be required for full effectiveness against the tougher walls of fungal spore cells and the like.

Testing has shown that the composition passes the standard "555-challenge" test (see British Standard BS EN 1276:1997 and the French Afnor test). As an effective anti-viral and anti-bacterial cleansing agent, it may be categorised as a (2) category disinfectant in the system employed by the UK National Health Service, suitable for cleaning in "medium high risk" areas.

The invention claimed is:

1. A cleaning solution comprising:

(a) at least one long chain alkyl polyamine of the formula:

$$H_2N(CH_2)_3—NR—(CH_2)_3NH_2$$

wherein R is a linear or branched alkyl amine chain comprising 10 to 14 carbon atoms;

(b) at least one aliphatic alcohol;

(c) iodine;

(d) at least one amphoteric surfactant; and (e) at least one antioxidant;

wherein the solution is non-dangerous in accordance with European Dangerous Preparations Directive (99/45/EC) and Dangerous Substances Directive (67/548/EEC).

2. A solution according to claim 1, wherein R is a linear alkyl chain.

3. A solution according to claim 2, wherein R comprises at least twelve carbon atoms.

4. A solution according to claim 1, wherein the solution further comprises a complexing agent adapted to form a complex with the iodine.

5. A solution according to claim 1, wherein the solution further comprises at least one buffering agent.

6. A means of destroying bacteria and/or inhibiting the ability of bacteria and/or viruses to replicate when said bacteria and/or viruses are present on a surface, the means comprising the application of a composition according to claim 1 to said surface wherein the composition is configured to rupture the phospholipid membrane of the bacteria or virus, the composition being further configured to cleave bacterial DNA and/or substantially permanently bind to bacterial DNA and viral DNA or RNA.

7. A means of inhibiting the ability of bacteria and/or viruses to replicate when said bacteria and/or viruses are present on a surface, the means comprising the application of a composition to said surface wherein the composition according to claim 1 is configured to substantially permanently encapsulate the bacteria or virus and prevent the replication of their genetic material.

8. The solution of claim 1, wherein $R=C_{12}$.

9. The solution of claim 8, wherein the at least one aliphatic alcohol is selected from the group consisting of ethanol and n-propanol.

10. The solution of claim 9, wherein the solution contains 10-30 vol. % of the at least one aliphatic alcohol.

11. The solution of claim 10, wherein solution includes up to about 0.5 wt. % iodine.

12. The solution of claim 11, wherein the solution further includes at least one wetting agent.

13. The solution of claim 12, wherein the at least one the wetting agent is selected from the group consisting of polyglycol ether, a polyethylene glycol ether, and a polypropylene glycol ether.

14. The solution of claim 13, further containing at least one of:

(i) a complexing agent, wherein the complexing agent is adapted to form a complex with the iodine, and;

(ii) a buffering agent.

15. The solution of claim 11, further containing at least one of:

(i) a complexing agent, wherein the complexing agent is adapted to form a complex with the iodine, and;

(ii) a buffering agent.

* * * * *

UNITED STATES PATENT AND TRADEMARK OFFICE
CERTIFICATE OF CORRECTION

| | | |
|---|---|---|
| PATENT NO. | : 7,915,216 B2 | Page 1 of 1 |
| APPLICATION NO. | : 10/556481 | |
| DATED | : March 29, 2011 | |
| INVENTOR(S) | : Christopher Malyszewicz | |

It is certified that error appears in the above-identified patent and that said Letters Patent is hereby corrected as shown below:

Title Page

Item (30) Foreign Application Priority Data, in the bibliographic data of the issued patent: insert --July 30, 2003 (GB) PCT/GB03/03296--

Col. 8, claim 7, Line 29-35
Replace claim 7 with the following claim:

--7. A means of inhibiting the ability of bacteria and/or viruses to replicate when said bacteria and/or viruses are present on a surface, the means comprising the application of a composition according to claim 1 to said surface wherein the composition is configured to substantially permanently encapsulate the bacteria or virus and prevent the replication of their genetic material, wherein the solution of claim 1 is provided.--

Signed and Sealed this
Thirty-first Day of July, 2012

David J. Kappos
*Director of the United States Patent and Trademark Office*